, LLC

(12) United States Patent
Lobedann et al.

(10) Patent No.: US 10,022,463 B2
(45) Date of Patent: Jul. 17, 2018

(54) DEVICE AND METHOD FOR CONTINUOUS VIRUS INACTIVATION

(71) Applicant: Bayer Aktiengesellschaft, Leverkusen (DE)

(72) Inventors: Martin Lobedann, Köln (DE); Stephan Klutz, Leverkusen (DE); Safa Kutup Kurt, Dortmund (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 15/125,130

(22) PCT Filed: Mar. 6, 2015

(86) PCT No.: PCT/EP2015/054698
§ 371 (c)(1),
(2) Date: Sep. 9, 2016

(87) PCT Pub. No.: WO2015/135844
PCT Pub. Date: Sep. 17, 2015

(65) Prior Publication Data
US 2016/0375159 A1  Dec. 29, 2016

(30) Foreign Application Priority Data

Mar. 11, 2014  (EP) .................................... 14158845

(51) Int. Cl.
*A61L 2/00* (2006.01)
*A61L 2/10* (2006.01)
(52) U.S. Cl.
CPC .............. *A61L 2/0088* (2013.01); *A61L 2/10* (2013.01); *A61L 2202/15* (2013.01); *A61L 2202/21* (2013.01)

(58) Field of Classification Search
CPC ................................ A61L 2/0088; A61L 2/10
See application file for complete search history.

(56) References Cited

U.S. PATENT DOCUMENTS 2,530,648 A    11/1950  Cahenzli
3,926,556 A *  12/1975  Boucher .................. A23C 3/07
                                                         250/435

(Continued)

FOREIGN PATENT DOCUMENTS

EP    0378716 A1    7/1990
EP    0944431 B1    8/2000

(Continued)

OTHER PUBLICATIONS

Saxena et al. (1983) "Effect of Coil Pitch and Cross-Sectional Ellipticity on RTD for Diffusion-Free Laminar Flow in Coiled Tubes," Chemical Engineering Communications, 23(4-6): 277-289.

(Continued)

*Primary Examiner* — Regina M Yoo
(74) *Attorney, Agent, or Firm* — McBee Moore Woodward & Vanik IP, LLC

(57) ABSTRACT

The invention provides an apparatus and a process for continuous virus inactivation. The apparatus for continuous virus inactivation in a product stream comprises a tube or hose 1 having an inlet 4 and an outlet 5 in each case connected to a product flow line 8 for conveying the product stream, where the tube or the hose 1 is curved and/or helically coiled with a number n of windings around a coil axis h and has one or more changes in direction and/or bends 2 in the coil axis h having an angle α of from 45° to 180° to alter the direction of action of the normals of the centrifugal force and the apparatus is characterized by a Dean number>0 and a torsion parameter>0.

3 Claims, 9 Drawing Sheets

(56) References Cited

U.S. PATENT DOCUMENTS

| | | |
|---|---|---|
| 6,399,031 B1 | 6/2002 | Herrmann et al. |
| 7,337,835 B2 | 3/2008 | Nigam |
| 7,420,183 B2 | 9/2008 | Kaiser et al. |
| 7,651,660 B2 | 1/2010 | Kaiser et al. |
| 2006/0162912 A1 | 7/2006 | Nigam |
| 2006/0257877 A1* | 11/2006 | Anderle ................ A61L 2/0011 435/6.18 |

FOREIGN PATENT DOCUMENTS

| | | |
|---|---|---|
| EP | 1339643 B1 | 1/2008 |
| EP | 1914202 A1 | 4/2008 |
| EP | 1916224 A1 | 4/2008 |
| EP | 1464342 B1 | 10/2009 |
| WO | WO-1998/026236 A2 | 6/1998 |
| WO | WO-02/38191 A2 | 5/2002 |

OTHER PUBLICATIONS

Saxena et al. (1984). "Coiled Configuration for Flow Inversion and Its Effect on Residence Time Distribution," AIChE Journal, 30(3): 363-368.

Sofer (2003). "Virus Inactivation in the 1990s—and into the 21st Century," Part 4, Culture Media, Biotechnology Products, and Vaccines, BioPharm International, pp. 50-57.

Vashisth et al. (2008). "Liquid-Phase Residence Time Distribution for Two-Phase Flow in Coiled Flow Inverter," Ind. Eng. Chem. Res. 47:3630-3638.

\* cited by examiner

DEVICE AND METHOD FOR CONTINUOUS VIRUS INACTIVATION

CROSS REFERENCE TO RELATED APPLICATIONS

This application is the national stage of International Application No. PCT/EP2015/054698, filed internationally on Mar. 6, 2015, which claims the benefit of European Patent Application No. 14158845.9, filed on Mar. 11, 2014, the disclosures of which are hereby incorporated by reference in their entireties for all purposes.

The present invention relates to an apparatus and a process for continuous virus inactivation. In particular, the invention relates to an apparatus and a process for continuous virus inactivation in a residence loop at a low pH.

Biopharmaceutical production processes require various orthogonal steps for virus reduction. A frequently used method of inactivating (enveloped) viruses is contact with an acidic medium, Virus inactivation at a low pH in the batch mode is known and frequently employed in the biopharmaceutical production of active substances, e.g. antibodies (Sofer 2003, Virus Inactivation in the 1990s—and into the 21st Century. Part 4. BioPharm International). Here, the material to be inactivated, viz, a liquid which potentially contains the active viruses, is introduced into a suitable vessel, brought to a pH of ≤4 by means of an acidic solution, homogenized if necessary and allowed to stand for the required time. The inactivation of the viruses is effected by contact of the viruses with the acidic solution for a particular product- and process-dependent time. The entire content of the bag thus experiences inactivation with a virtually identical residence time and the virus reduction achieved in each fluid element of the vessel is consequently also virtually identical.

If a process for the production of biopharmaceutical and biological products, in particular pharmaceutical antibodies, were to be operated in the continuous mode, the required hold time for virus inactivation would have to be achieved. For the purposes of the present patent application, continuous virus inactivation means that the introduction of feed stream into the virus inactivation module and the discharge of the product stream from the virus inactivation module occur without pauses. Continuous operation of a production plant comprising at least one bioreactor means, for the purposes of the present patent application, that the introduction of feed stream into the bioreactor and the discharge of the product stream from the production plant occur without pauses, with some process steps being able to operate semicontinuously.

The required hold time (=residence time for virus inactivation could be achieved in a residence loop. Here, laminar flow in the residence loop can be problematical. In laminar flow through a tube, a parabolic velocity profile is established, which results in a broad residence time distribution (FIG. 1). Since the maximum velocity in the center of the flow through the tube is twice the average velocity but the velocity at the tube walls is zero (adhesion condition), a very broad residence time distribution occurs in these cases. The residence times obtained in this way range from half the average residence time (due to the fast-flowing fluid elements in the middle of the tube) to an infinitely long residence time (due to die adhering fluid elements in the vicinity of the wall). Since, firstly, a minimum residence time is necessary for effective inactivation of the viruses but, secondly, long residence times at a low pH could damage the product (e.g. a protein), achievement of a narrow residence time distribution in continuous operation is indispensible. In this case, a change from the laminar flow situation to turbulent plug flow having a uniform residence time is not an acceptable alternative. Turbulent flows require high flow velocities. If the long residence times usual for virus inactivation at a low pH (for example 60-120 minutes) are then to be achieved, undesirably large plants result.

One way of carrying out continuous virus inactivation is irradiation with UV-C WO2002038191, EP1339643B1, EP1464342B1, EP1914202A1 and ER1916224A1 describe the use of a helical residence loop in which the material to be inactivated is irradiated with UV-C light and the viruses present are consequently inactivated. When a fluid flows through a helically coiled tube, centrifugal force acts on the fluid. The centrifugal forces induce secondary flows (known as Dean eddies), which leads to improved radial mixing and thus more homogeneous irradiation of the material to be inactivated. The helix structure used in the sources mentioned is a straight helical coil without changes in direction of the axis of the helix. For use in continuous virus inactivation at a low pH, the use of a straight helix structure as is used in UV-C irradiation is not practicable since the residence time distribution may well be narrower than in the case of a straight tube through which laminar flow occurs but is still too broad. Owing to the still comparatively broad residence time distribution, this geometry would still require a large plant for pH virus inactivation.

Since firstly a required minimum residence time has to be achieved for each fluid element and secondly the product, in particular a protein product, can be damaged at a low pH, it is necessary to achieve very narrow residence time distributions for a pH-based virus inactivation.

Nigam et al. [U.S. Pat. No. 7,337,835B2, AIChE Journal (1984), Vol. 30, No. 3, p. 363-368, Chem. Eng. Comm. (1983) 23, 4-6, p. 277-289] teach that in the case of flow through helical coils, bending of the axis of the helical coils brings about a change in the direction of action of the normals of the centrifugal force on the fluid. The narrowest residence time distributions can, according to Nigam et al., be obtained at a value for the Dean number of $Dn \geq 3$, while at $Dn < 3$ a broadening of the residence time distribution is observed. This technique was referred to by the authors as "coiled flow inverter" (CFI). The principle of the CFI is shown in FIG. 2. The centrifugal force caused by the helical tube geometry generates secondary flows as a result of which narrow residence time distributions can be realized in heat exchangers even in the case of laminar flow. Nigam et al. teach that implementation of 90° bends produces considerably narrower residence time distributions than in the straight helix or the straight tube through which laminar flow occurs. Nigam et al. also teach that the residence time distribution is narrower, the more bends are used. With an increasing number of bends, an approximation to the residence time distribution of a flow tube through which turbulent flow occurs and which has a plug flow profile is obtained.

The applicability of this tube geometry to processes which at the same time require a long residence time and a narrow residence time distribution, e.g. virus inactivation at a low pH, is not examined or mentioned. A long residence time is irrelevant to the provision of a heat exchanger.

It was therefore an object of the present invention to provide a novel, simple and inexpensive solution which makes it possible to achieve the required residence time in a residence loop through which continuous flow occurs for continuous virus inactivation at a low pH with a narrow residence time distribution.

The invention achieves this object by provision of an apparatus for the continuous inactivation of viruses in a product stream, which comprises a tube or hose 1 having an inlet 4 and an outlet 5 in each case connected to a product flow line 8 for conveying the product stream, where the tube or the hose 1 is curved and/or helically coiled with a number n of windings around a coil axis h and has one or more changes in direction and/or bends 2 in the coil axis having an angle α of from 45° to 180° to alter the direction of action of the normals of the centrifugal force and the apparatus is characterized by a Dean number >0 and a torsion parameter >0.

The apparatus can, apart from a Dean number ≥0, also have a Dean number≥1, preferably ≥2 preferably ≥3, more preferably ≥4.

The apparatus can, apart from a torsion parameter of ≥0, also have a torsion parameter ≥100, ≥200, ≥300, ≥400, particularly preferably >500.

In a particularly preferred embodiment, the apparatus has a Dean number ≥3 and a torsion parameter ≥500.

The tube or the hose 1 is preferably helically coiled around the coil axis h. The cross section of the coil axis is usually round.

An example of a curved configuration is known from EP094443181B1, in particular in FIG. 5 to which are hereby incorporated by reference together with their description.

The apparatus of the invention can comprise a holding stand 6 which bears one or more frames 3. As an alternative, the holding stand forms the coil axis. The frames and/or the holding stand can be hollow or fitted. If the hose or the tube 1 has a high strength and stiffness, a self-supporting structure is also possible.

As regards the dimensions of the plant, the teaching of Nigam et al. is incorporated by reference: U.S. Pat. No. 7,337,835B2, AIChE journal (1984), Vol. 30, No. 3, p. 363-368, Chem. Eng. Comm. (1983) 23, 4-6, p. 277-289. In particular, Nigam et al. teach that increasing the mixing in the radial direction, which results in a narrowing of the residence time distribution, occurs even at an angle α of from 45° to 180°, but preferably in a range from 40° to 120° and in particular 90°. FIG. 2 shows the principle of the CFI according to Nigam et al. and its design parameters for the particular case of α=90°. It is possible to see how die flow profile changes as a function of the direction of the helical coil.

As design parameters, mention may be made of:
hose internal diameter $d_i$
pitch distance $p$
coil tube diameter $d_{ct}$
coil diameter $d_c$
number of windings per arm n (an arm is the region of a straight helical coil between two successive bends)
angle α of the bends
number of bends (in the frame shown 4 bends per frame)

The dimensionless parameters describing the system are the Reynolds number Re, the Dean number Dn and the torsion parameter T.

The Reynolds number Re is calculated according to:

$$Re = \frac{\rho \cdot \bar{v} \cdot d_i}{\eta}$$

Using the density of fluid ρ, the average flow velocity $\bar{v}$ and the dynamic viscosity η.

The Dean number Dn is calculated according to:

$$Dn = Re \cdot \sqrt{d_i / d_c}$$

The torsion parameter T is calculated according to:

$$T = \frac{\pi \cdot r_c \cdot Re}{p}$$

Nigam et al. teach that the best results can be achieved when the pitch distance is minimized, the angle α=90°, the Dean number is at least 3 and the torsion parameter is ≥500. For stable secondary flows to be able to form in the helix, each arm should also have at least two complete windings. [AIChE Journal (1984), Vol. 30, No. 3, p. 363-368] and [Chem. Eng. Comm, (1983) 23, 4-6, p. 277-289].

The dimensioning of the apparatus of the invention is usually carried out as follows:

In a first step, the desired volume flow is set down.
On this basis, possible dimensions are calculated using the abovementioned fomulae subject to the condition that the Dean number is preferably ≥3 and the torsion parameter is preferably ≥500.

The curves produced are shown by way of example for a volume flow of 3 ml/min in FIG. 4. The suitable dimensions for the apparatus may be found according to Nigam et al. to the left of the advantageous curve for torsion parameter=500 and to the left of the advantageous curve for a Dean number=3. The most appropriate tube internal diameters and coil tube diameter are selected so as to be optimized in terms of in particular, the space requirement. Here, the hose internal diameter is selected so that the required minimum residence time is achieved. The coil tube diameter should then be made as small as possible. The reason for this is that, according to Nigam et al., the residence time distribution becomes narrower, the more bends are installed in the residence section. For a defined hose length of the residence section and a fixed number of windings per helix, it is possible to install more bends, the smaller the coil tube diameter. As an approximation, the number of bends $n_{Bend}$ of the residence section having the length L can be calculated, where $n_{arm,frame}$ is the number of arms per frame, $n_{winding,arm}$ is the number of windings per arm, π is the number pi and $d_c$ is the coil diameter, where $d_c=d_{ct}+d_o$: here, $d_o$ is the external diameter of the hose.

$$n_{bend} = \frac{L}{n_{bend,frame} \cdot n_{winding,arm} \cdot \pi \cdot d_c} - 1$$

According to the invention, the abovementioned parameters were by way of example selected for a test plant for continuous virus inactivation at a volume flow of about 3 ml/min. The required hose length is obtained with the aid of the minimum residence time required for the particular case and the internal hose diameter selected. In the next step, the coil tube diameter is selected so that the condition that both the Dean number ≥0 and the torsion parameter ≥0, preferably both the Dean number ≥2, preferably ≥3, and the torsion parameter ≥300, preferably ≥500, is satisfied. In this respect, see FIG. 4.

The internal diameter $d_i$ of the tube or hose 1 is usually from 1 to 30 mm, preferably in the range from 3 to 6 mm. For example, a commercial tube/commercial hose having an internal diameter of 3 mm was used in the test plant. The minimum possible coil tube diameter for this case was subsequently selected. The smaller the coil tube diameter selected, the more bends can be realized for a given hose length. Since an increasing number of bends narrows the residence time distribution, this number should always be made as large as possible.

The total length L and the internal diameter of the tubes/hoses 1 are adapted to the dimensions of the total plant/flow rate of the plant so that the residence times required in the particular case are adhered to.

In the case of a plant having the abovementioned size, the tube or the hose 1 usually has a total length L of from 1 to 200 m, preferably from 50 to 100 m.

The number of windings n between two changes in direction and/or bends 2 is usually at least 2-20, preferably from 5 to 15, particularly preferably 10, where the number of windings is selected so that the unit occupies a very small volume.

If the holding stand forms the coil axis or the hose or the tube 1 is self-supporting, the coil axis usually has from 2 to n changes in direction and/or bends 2, where n can be any desired number. The number n is selected so that the total length L of the tubes/hoses 1 is wound around the unit and occupies a very small volume.

If frames are used as coil axis, each frame 3 usually has from 2 to 6 changes in direction and/or bends 2. Preference is given to square frames (90° bends) as shown in FIG. 2, without being restricted thereto. One or more frames are usually fastened above one another on the stand 6 until the total length L of the tube/hose 1 is wound around the unit and occupies a very small volume.

The narrow residence time distribution achieved in this way makes it possible to achieve the required removal of viruses at a particular product- and process-dependent minimum residence time without reaching the maximum, likewise product- and process-dependent residence time which would lead to damage to the product (typically from 30 minutes for pH-sensitive products to 120 minutes for less sensitive products). The required residence time and also the maximum residence time are product-dependent and are typically determined experimentally. The maximum residence tune is optimized so that the product suffers minimal damage in order to keep the need for downstream purification steps as low as possible. The residence time distribution approaches the average residence time of the ideal flow tube reactor. In this way, it is possible to ensure effective continuously operated virus inactivation at a low pH, the results or virus removal and product quality of which would be comparable to virus inactivation in a batch process.

Particularly when utilizing frames on a stand, simple, scaleable and inexpensive manufacture of the apparatus (also for single use) is possible. The hose/the tube is only wound in the required way around the frames either after or before the hose/the tube has been sterilized. After use of the unit in the process, the hose/the tube can be detached from the frame and disposed of or cleaned (if multiple use is desired). The angles of the bends should have defined values. The position of the hose/tube should likewise be defined, e.g. for simple and reproducible cods by guide notches milled into the frames. For operation in a plant, it is in this way ensured that the plant has the same effectiveness in each production run.

Furthermore, the apparatus can be sterilizable, preferably autoclavable or gamma-irradiatable. To attain this property, preference is given to using a hose which corresponds to the relevant quality requirements, e.g. medical quality (USP class VI). The apparatus of the invention can preferably be autoclaved or gamma-sterilized, which makes a sterile operation possible.

Furthermore, the invention provides a process for the continuous virus inactivation of a product stream, which comprises the following steps:
   a) provision of the product stream to be inactivated,
   b) introduction of the product stream into the inlet 4 of a tube or hose 1 having an inlet 4 and an outlet 5, where the tube or the hose 1 is carved and/or helically coiled with a number n of windings around a coil axis h and has one or more changes in direction and/or bends 2 in the coil axis having an angle α of from 45° to 180° to alter the direction of action of the normals of the centrifugal force, where the apparatus is characterized by a Dean number >0 and a torsion parameter >0,
   c) flow of the product stream through the tube or the hose 1 under virus-inactivating conditions and
   d) exit from the tube or the hose 1 through the outlet 5.

A product stream of liquid which can contain both product and potentially viruses to be inactivated is produced in step a).

The apparatus in step b) of the process of the invention can, apart from a Dean number ≥0, also have a Dean number ≥1, preferably ≥2, preferably ≥3, more preferably ≥4.

The apparatus in step b) of the process of the invention can, apart from a torsion parameter of ≥0, also have a torsion parameter ≥100, ≥200, ≥300, ≥400, particularly preferably ≥500, In a particularly preferred embodiment, the apparatus in step b) of the process of the invention has a Dean number ≥3 and a torsion parameter ≥500.

As possible virus-inactivating conditions for step c), mention may be made of a pH ≥4, UV treatment or thermal treatment.

In step a), the pH of the product stream is preferably set to a value of ≥4 if the pH of the material to be inactivated does not already have the required value. In this case, the pH is preferably set to ≥5 by means of a base after step d) in order to stop virus inactivation.

Setting of the pH of the solution to be inactivated to ≥4 can, for example, be effected by addition of HCl solution. The addition is typically carried out upstream of the apparatus of the invention. The pH of the product stream before entry into the apparatus for virus inactivation is measured by means of the sensor pH0501. (FIG. 8). This pH sensor usually does not have regulating tasks. The recording of the pH signal serves merely for monitoring of the process.

If the production process requires one or more adjustments of the pH, the apparatus for virus inactivation is connected to a unit for setting the pH. It is usual to use two units for setting the pH, the first before the inactivation in order to bring the product stream to a pH ≥4 (step 1)) and a further one after the inactivation in order to neutralize the product stream (step d).

In step c), the desired contact time (=residence time) between acidic solution and any viruses present is achieved.

As base in step d), it is possible to use, for example, sodium hydroxide solution (NaOH).

The process can be carried out as a batch operation and as a continuous production process and thus be integrated into a batch process and into a continuous process.

If the apparatus for virus inactivation is integrated into a continuous production process, preference is given to one or more units for setting the pH in which the product stream flows through a recirculation loop. FIG. 8 shows the virus inactivation and a subsequent neutralization by way of example, without being restricted thereto. M0503 conveys the product stream into the bag B0502 where the pH after leaving the virus inactivation is set to a value of ≥5. The contents of the bag B0502 are conveyed by the recirculation pump M0504 through the recirculation loop into the pH sensor pH0502 which measures the pH of the product stream. Downstream of the sensor, the adjusting agent for modifying the pH is fed in. The pump for the adjusting agent is M0505 and is regulated via the associated sensor pH0502.

In the process of the invention, the product stream to be inactivated is usually a solution from a bioreactor, in particular a protein or peptide solution and very particularly preferably an antibody solution.

The technical advantage of the continuous virus inactivation according to the invention over the virus inactivation in the batch mode which is usual in the prior art is the ability to be integrated into a continuous work-up process, also referred to as "downstream processing" without having to alter die mode of operation of the process. Here, there is no change in process operation from batch to continuous and back again, but instead the entire "downstream processing" or the entire production process (upstream and downstream) can be operated continuously.

The patent application further provides a production plant comprising one or more apparatuses according to the invention for the continuous inactivation of viruses in a product stream and preferably at least one unit for setting the pH.

The present invention including preferred embodiments is illustrated in conjunction with the following drawings and examples, without being restricted thereto. The embodiments can be combined in any desired way, unless the context clearly indicates otherwise.

The reference numerals used are:
1=curved and/or helically coiled tube or hose
2=changes in direction and/or bends 2 of the coil axis h at an angle α of from 45° to 180°
3=frame
4=inlet
5=outlet
6=holding stand
7=base
8=product flow line FIG. 1 shows a parabolic flow profile of the tube through which laminar flow occurs (top: longitudinal section of the tube). Lines of the same velocity in the flow direction in the tube through which laminar flow occurs (bottom: cross section of the tube).
a=tube wall
b=axial axis of the tube in the flow direction
c=radial axis
d=lines of the same flow velocity in the flow direction FIG. 2 shows the principle and design parameters of the CFI with depiction of the flow profile. Lines of the same velocity in the flow direction are shown. Flow profiles were taken from: Ind. Eng. Chem. Res. (2008), 47, 10, pp. 3630-3638
hose internal diameter $d_i$
hose external diameter $d_o$
pitch distance p
coil tube diameter $d_{ct}$
coil diameter $d_c$
angle α of the bends e=direction of action of the centrifugal force
f=direction of flow through the helical coils
g=flow direction of the fluid in the helical coil
h=coil axis/axis of the helix FIG. 3 shows the results of the examination of the residence time behaviour of the apparatus for the continuous inactivation of viruses having various numbers of bends at a volume flow of 3 ml/min compared to a straight tube through which laminar flow occurs and an ideal flow tube. (Bend=90° change in direction for altering the normals of the direction of action of the centrifugal force on the flow. The dimensionless concentration of 1 corresponds to a concentration of vitamin B12 of 0.25 g/l).

Figure 6:
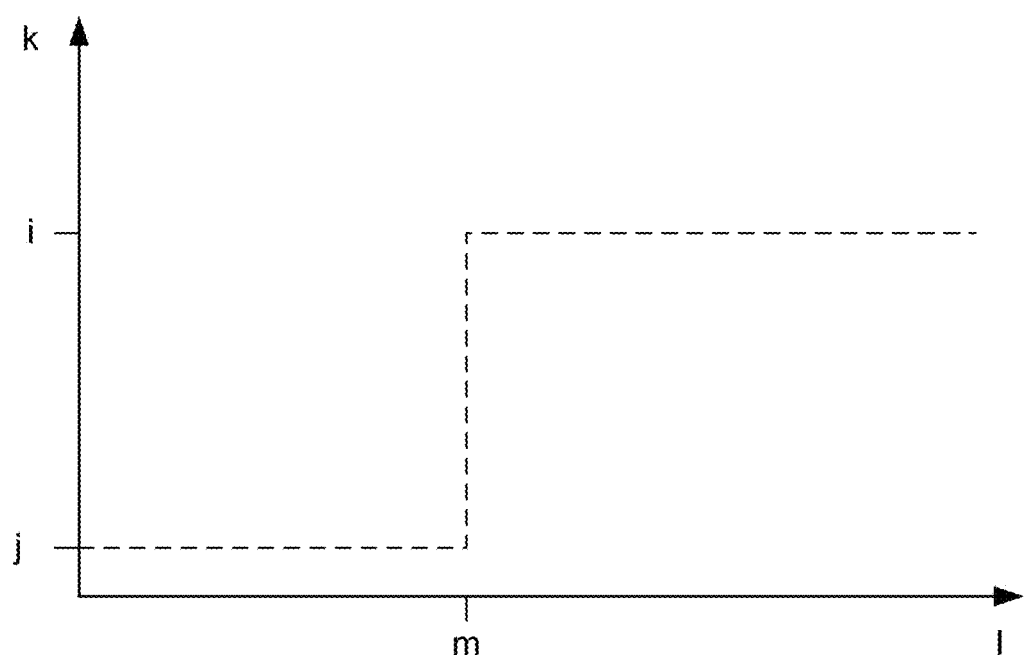
Figure 7:
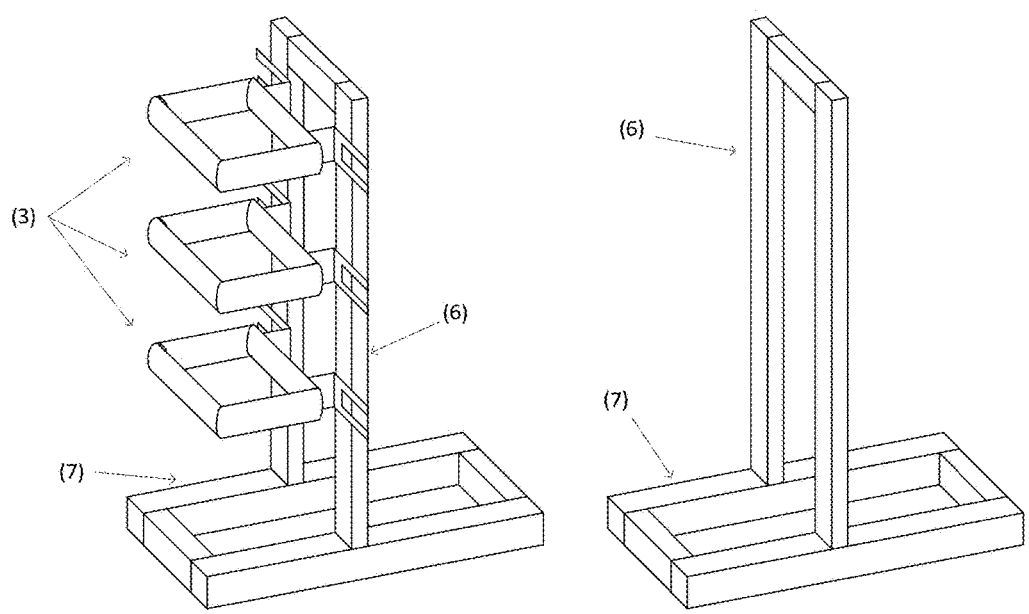

FIG. 6 shows the step function of the tracer solution introduced in Example 1 at the inlet into the apparatus for virus inactivation.
i=time axis
j=axis of the UV signal
k=point in time of the introduction of the tracer substance at the inlet of the CFI FIG. 7 shows a drawing of the apparatus for continuous virus inactivation according to the example of the CFI. At left: holding stand with mounted frames. At right: holding frame without mounted frames.

Figure 8:
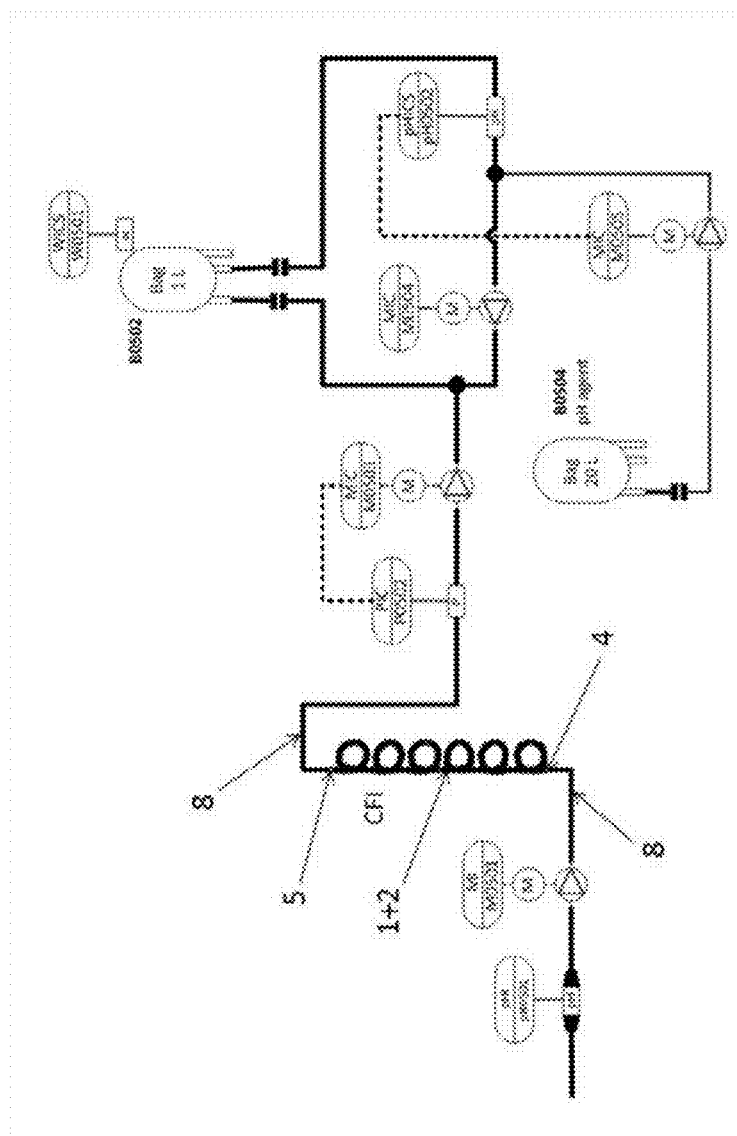

FIG. 8 Flow diagram of virus inactivation with subsequent adjustment of the pH, with the helically coiled tube 1 and its changes in direction and/or bends 2 being shown purely schematically.

Figure 9:
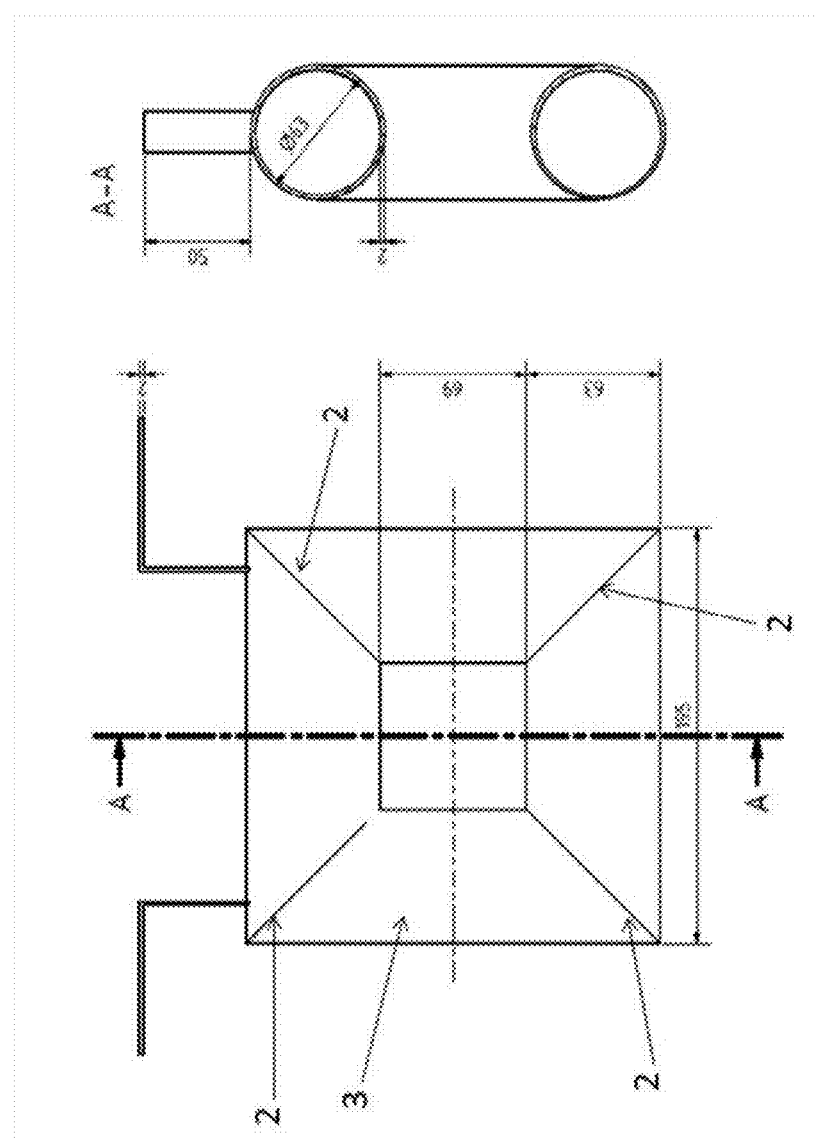

FIG. 9 Construction drawing of a frame from the experimental studies.

EXAMPLE 1

Figure 4:
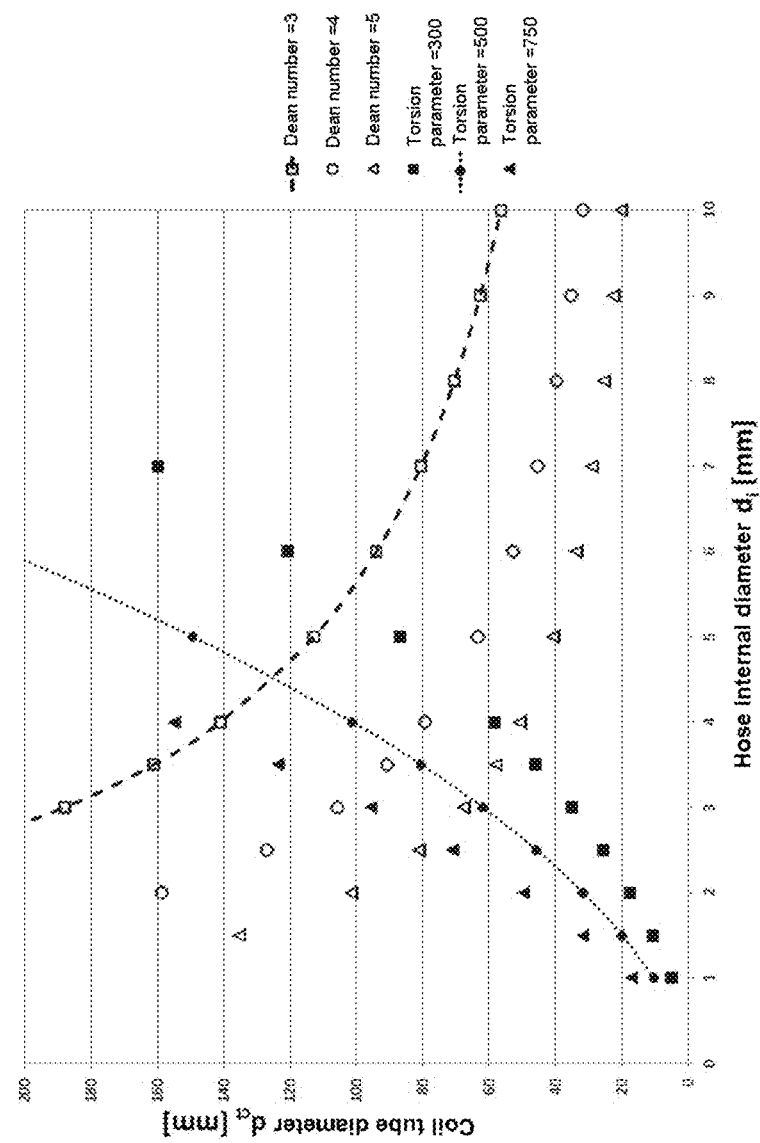
FIG. 4 shows the graph for designing the CFI at a volume flow of 3 ml/min.

The design of the frames was carried out as shown in FIG. 4. This graph was constructed for a flow rate of 3 ml/min and shows the range in which the design parameters hose internal diameter and coil tube diameter can be varied in order to adhere to the required conditions of Dean number ≥3 and torsion parameter ≥500 in the construction of the frames.

A hose internal diameter of 3 mm was selected for the experimental studies. The coil tube diameter was then chosen as 63 mm so that the hose length wound up on each frame could be minimized.

Figure 3:
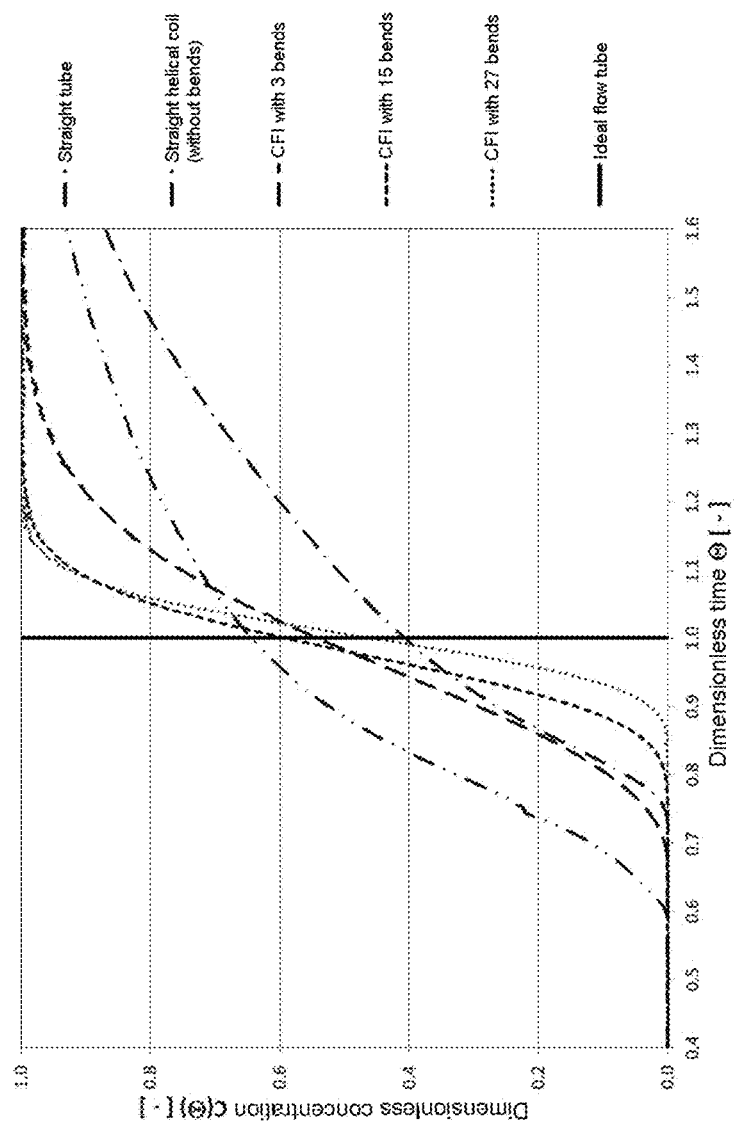

The dimensions of the structure used in the experimental studies, the results of which are shown in FIG. 3, are:

Frame diameter (coil tube diameter) 63 mm; outer edge length of the frames 195 mm. Hose internal diameter 3 mm; hose external diameter 5 min. The frames were constructed as shown in FIG. 9. Each arm always had 11 windings having a minimal pitch distance, so that 9.5 m of hose were wound up on a frame. Minimal pitch distance means that the hose is in contact in the helix. For the case "3 bends", one frame was used. Consequently, 9.5 m of hose were wound on for this experiment. For the case "15 bends", four frames were used. A total of 38 m of hose were wound onto four frames. For the case "27 bends", seven frames were used. A total of 66.5 m of hose were wound onto seven frames. The hose length used per frame is, under the assumption of a constant number of windings per arm, proportional to the coil tube diameter. The hose external diameter was 5 mm in the case of the hose used.

Figure 5:
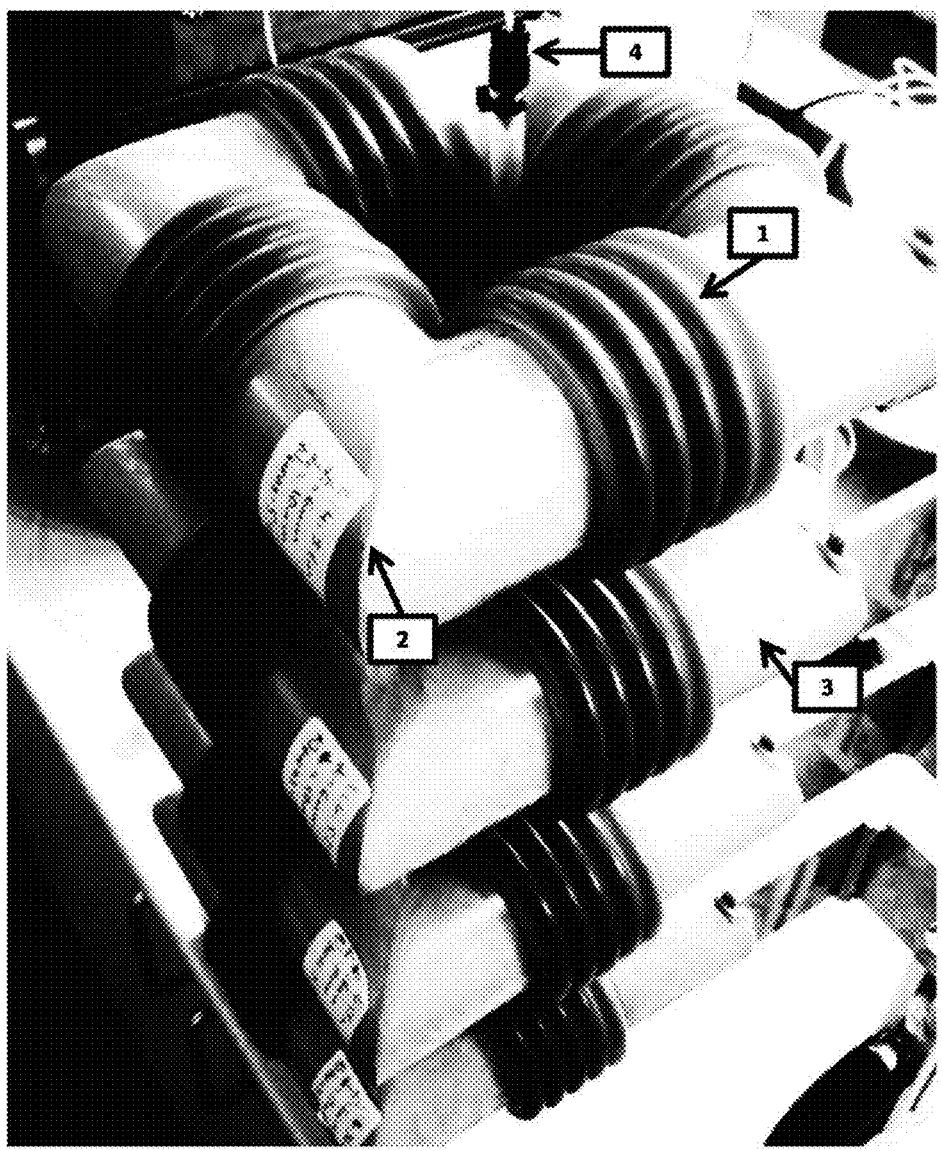
FIG. 5 shows a photograph of the apparatus as used in the experiments for residence time measurement (4 frames).

FIG. 5 shows the arrangement of the frames and hose coils as employed in the experiments for residence time measurement. However, for reasons of clarity, a larger hose diameter hose internal diameter 6 mm) was used for this figure. Consequently, the 11 windings per arm used in the experiments were not possible.

Figure 2:
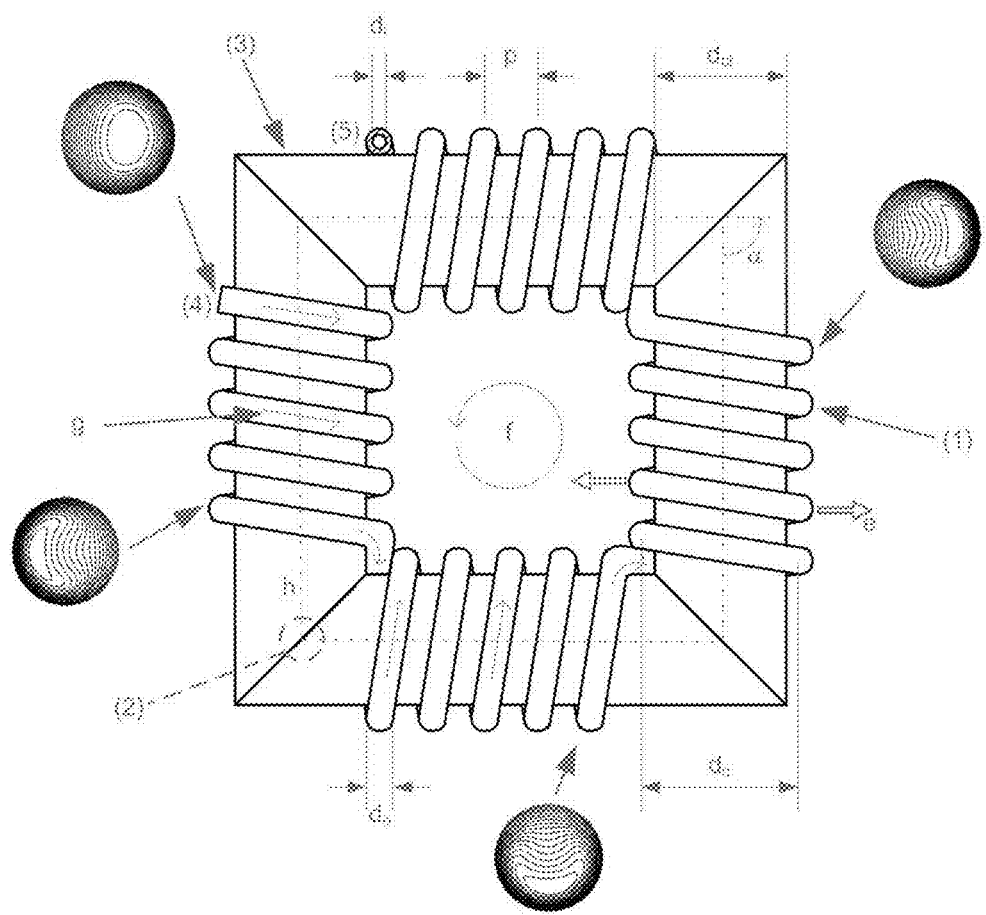

In the experimental structure, the hose used in the respective experiments as shown in FIG. 2 and FIG. 5 was firstly wound up separately on each frame. The frames with the hoses were subsequently arranged above one another on a holding stand. Here, the outlet of the upper frame was joined to the inlet of the frame underneath, an that the hose coil would run through the frame from the top downwards. As an alternative, flow can also be from the bottom upwards or horizontally.

The experiments for measurement of the residence time in the apparatus for continuous virus inactivation (CHI) were carried out with the aid of a UV measurement at the outlet of the system. The flow rates were always 3 ml/min, the internal diameter of the silicone hoses used was 3 mm, the external diameter of the hoses was 5 mm. The external diameter of the frames around which the hoses were coiled was 63 mm (coil tube diameter). A vitamin B12 solution having a concentration of 0.25 g/l was used as tracer substance since vitamin B12 absorbs UV light at a wavelength of 280 nm and is thus suitable as indicator.

Firstly, the CFI was flushed with distilled water. At the point in time k, a change was made to the tracer solution at the inlet of the virus inactivation and recording the measurement signal of the UV sensor was commenced (see FIG. 6). A step function of the tracer solution was then applied to the system. When the UV signal at the outlet of the system corresponded to the UV signal of the tracer solution, the experiments could be stopped since the system was completely filled with tracer solution from this point in time and the response of the system to the step function had thus been completely recorded.

For the various residence time curves recorded to be able to be compared with one another, the measurements were normalized to dimensionless parameters. The time was normalized to the average residence time τ;

$$\tau = \frac{V}{\dot{V}}$$

where V is the holdup volume of the residence section and $\dot{v}$ is the volume flow. The dimensionless concentration was Obtained by normalizing the measured UV signal to the maximum UV signal recorded (at a vitamin B12 concentration of 0.25 mg/l). A vitamin B12 concentration of 0.25 mg/l consequently gives a dimensionless concentration of 1. The U signal of distilled water leads to a dimensionless concentration of 0.

The results of the measurements are shown in FIG. 3. The residence time distribution of the straight tube through which laminar flow occurs was determined analytically according to the following equation. F(θ) is the dimensionless concentration and θ is the dimensionless time.

$$F(\theta) = 1 - \frac{1}{4 \cdot \theta^2}$$

Figure 1:
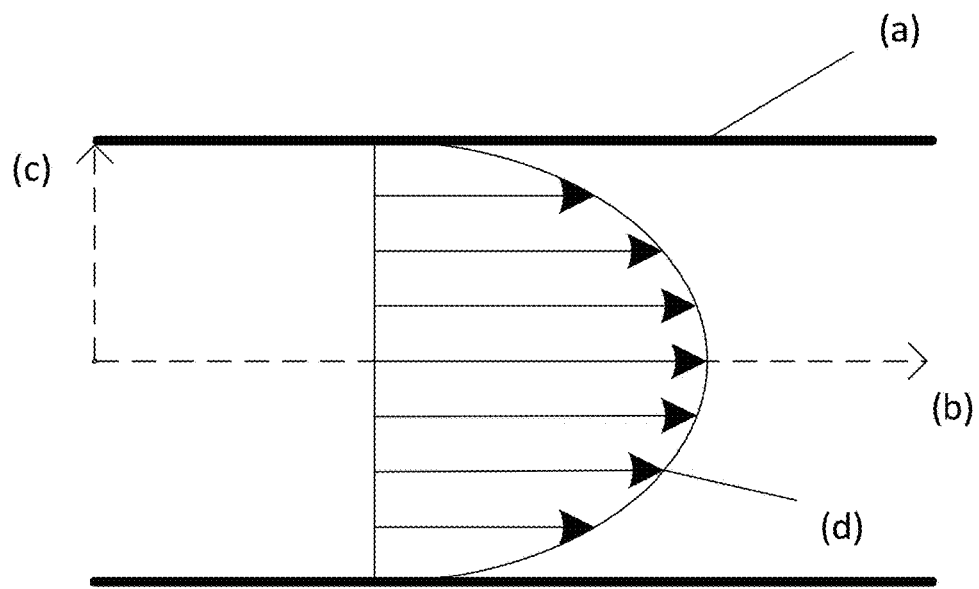
Figure 1:
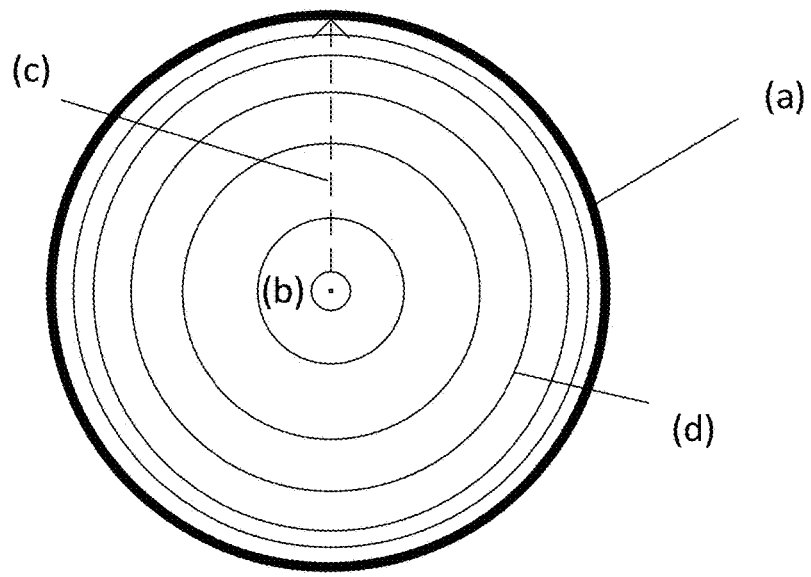

The straight tube through which laminar flow occurs has, owing to its parabolic flow profile, a comparatively broad residence time distribution. The fluid elements flow significantly faster in the center of the tube than in the region close to the wall (see FIG. 1).

If, on the other hand, the hose is helically coiled, the centrifugal force brings about mixing of the system in the radial direction. As a consequence of this, slowly flowing fluid elements which are relatively close to the axis of the helix move outward and displace the elements located there in an inward direction. As a result of the implementation of bends, the secondary flows caused by the centrifugal force are built up afresh, which leads to improved radial mixing. FIG. 2 shows how the flow profile turns through 90° after each 90° bend. As can be seen from FIG. 3, a significant narrowing of the residence time distribution can be achieved by the use of bends.

The best result achieved in the experiments occurred when using the CFI having 27 bends (a greater number of bends was not examined). An approximation to the residence time distribution of an ideal flow tube was obtained. It is probable that additional bends would narrow the residence time distribution further. The technique described is therefore suitable as process for continuous virus inactivation.

The work leading to this patent application was supported pursuant to the financial assistance agreement "Bio.NRW: MoBiDiK—Modulare Bioproduktion—Disposable and Kontinuierlich" within the framework of the European Fund for Regional Development (EFRE).

The invention claimed is:

1. A process for continuous virus inactivation of a product stream using an apparatus, which comprises the following steps:
    a) provision of the product stream to be inactivated,
    b) introduction of the product stream into an inlet (4) of a tube or hose (1) having the inlet (4) and an outlet (5), where the tube or hose (1) is curved and/or helically coiled with a number n of windings around a coil axis h and has one or more changes in direction and/or bends (2) in the coil axis having an angle α of from 45° to 180° to alter the direction of action of normals of a centrifugal force, where the apparatus is characterized by a Dean number >2 and a torsion parameter >100,
    c) flow of the product stream through the tube or hose (1) under virus-inactivating conditions, and
    d) exit from the tube or hose (1) through the outlet (5), wherein the pH of the product stream in step a) is set to a value of ≤4 and wherein the pH is set to ≥5 after step d) in order to stop virus inactivation.

2. The process according to claim 1, characterized in that the apparatus in step b) is characterized by a Dean number ≥3, and a torsion parameter ≥300.

3. The process according to claim 1, characterized in that the product stream comprises a solution of macromolecules, preferably a protein or peptide solution, particularly preferably an antibody solution.

* * * * *